US012788644B2

(12) United States Patent
Nilsson et al.

(10) Patent No.: US 12,788,644 B2
(45) Date of Patent: Nov. 10, 2026

(54) DISPOSABLE ABSORBENT HYGIENE ARTICLE

(71) Applicant: Essity Hygiene and Health Aktiebolag, Gothenburg (SE)

(72) Inventors: Lisa Nilsson, Gothenburg (SE); Yasha Asayesh, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 360 days.

(21) Appl. No.: 18/548,258

(22) PCT Filed: Mar. 2, 2021

(86) PCT No.: PCT/SE2021/050177
§ 371 (c)(1),
(2) Date: Aug. 29, 2023

(87) PCT Pub. No.: WO2022/186739
PCT Pub. Date: Sep. 9, 2022

(65) Prior Publication Data

US 2024/0156654 A1 May 16, 2024

(51) Int. Cl.
*A61F 13/15* (2006.01)
*A61F 13/49* (2006.01)
*A61F 13/56* (2006.01)

(52) U.S. Cl.
CPC .... *A61F 13/5638* (2013.01); *A61F 13/49014* (2013.01)

(58) Field of Classification Search
CPC .............. A61F 13/5633; A61F 13/4906; A61F 13/622; A61F 13/62; A61F 13/56; A61F 13/49; A61F 13/5638; A61F 13/49014
(Continued)

(56) References Cited

U.S. PATENT DOCUMENTS

2002/0151858 A1* 10/2002 Karami ............. A61F 13/49019 604/389
2005/0222551 A1 10/2005 Otsubo
(Continued)

FOREIGN PATENT DOCUMENTS

EP 2647360 A1 10/2013
WO 9514453 A2 6/1995

OTHER PUBLICATIONS

International Search Report & Written Opinion for International Application No. PCT/SE2021/050177; International Filing Date: Mar. 2, 2021; Date of Mailing: Nov. 1, 2021; 16 pages.
(Continued)

*Primary Examiner* — Jacqueline F Stephens
(74) *Attorney, Agent, or Firm* — CANTOR COLBURN LLP

(57) ABSTRACT

The disclosure relates to a disposable absorbent article having a longitudinal direction and a transverse direction (x), perpendicular thereto, including an absorbent assembly having a first portion, a second portion and opposing side edges extending in the longitudinal direction (Y) from the first portion, and two elastic side portions arranged at the second portion, with an elastic side portion extending beyond the side edges in the transverse direction, be fastened to the first portion when the absorbent article is worn. Each of the elastic side portions carries at least one fastener that at least partly overlaps the side portion, defining an overlapping region between the fastener and the elastic side portion, wherein the article includes a reinforcement material patch for each elastic side portion that is permanently attached to the elastic side portion, and the fastener is permanently attached to the reinforcement material patch.

23 Claims, 3 Drawing Sheets

(58) Field of Classification Search
USPC .......................................... 604/392, 391, 386
See application file for complete search history.

(56) References Cited

U.S. PATENT DOCUMENTS

| | | | | |
|---|---|---|---|---|
| 2005/0222552 | A1 | 10/2005 | Otsubo | |
| 2006/0129121 | A1* | 6/2006 | Erdman | A61F 13/5622 604/389 |
| 2009/0198206 | A1* | 8/2009 | Kline | A61F 13/15 604/386 |
| 2014/0358107 | A1 | 12/2014 | Bader et al. | |
| 2015/0290048 | A1 | 10/2015 | Sugiyama et al. | |
| 2018/0042785 | A1* | 2/2018 | Dalal | A61F 13/84 |

OTHER PUBLICATIONS

European Application No. 21929344.6-1102; European Search Report dated Oct. 7, 2024; 6 pages.

* cited by examiner

DISPOSABLE ABSORBENT HYGIENE ARTICLE

CROSS REFERENCE TO RELATED APPLICATIONS

This application is a National Stage Application of PCT/SE2021/050177, filed Mar. 2, 2021, which is incorporated by reference in its entirety herein.

TECHNICAL FIELD

The present disclosure relates to a disposable open-type absorbent hygiene article, such as a diaper or incontinence article.

BACKGROUND

Disposable absorbent hygiene articles, for example in the form of diapers and incontinence garments, are well known. Such articles are used for absorbing, distributing and storing various types of body exudates, for example urine, while providing a high level of comfort and sense of dryness to the wearer during use. A conventional disposable absorbent article is normally designed with an absorbent assembly comprising an absorbent core which is sandwiched between a top sheet and a back sheet.

The absorbent assembly may comprise a first portion and a second portion, defining a longitudinal extension of the article from the first portion to the second portion, and opposing side edges extending from said first portion to said second portion, defining a transverse extension between said side edges.

Some disposable absorbent hygiene articles, for example diapers and incontinence garments, comprise front and/or back side panels which extend beyond the side edges of the absorbent assembly. When the article is in a use position with the absorbent assembly positioned over the crotch of the wearer, the front and/or back side panels are configured to form at least part of a waist opening around the waist of the wearer, and leg openings for the legs of the wearer are formed between the side panels and the absorbent assembly.

An open-type absorbent hygienic article, such as an open-type diaper, is an article which is provided to a user in an open state and which is configured to be closed to form a closed state around the wearer's waist when the article is worn (in the use position). To this end, the front and/or back side panels may be provided with fasteners for closing the article around a wearer when the article is applied. The fasteners may be openable and re-closable to allow for reclosing of the article for example for inspection thereof after some time of use, or for adjustment of the size of the waist opening of the article.

As such, open-type absorbent articles differ from pant-type articles. Pant-type articles are provided to a user in a closed state and are pulled over the legs of the wearer when applied. In such articles, front and back side panels extending from the absorbent assembly are conventionally permanently joined to each other by means of a seam in each side of the article, so as to form a pant-like article with a waist opening and leg openings. A pant-type article may be removed either by pulling it down along the legs of the wearer, or by ripping open the article by destruction of its side seams. Pant-type articles are thus provided in fixed sizes.

WO 95/14453 describes examples of open-type absorbent articles.

There is a continuous need for improvement in open-type absorbent articles having side portions provided with fasteners as mentioned in the above. Such needs may relate to one or more of needs for improving comfort to the wearer, needs for ensuring reliable function of the article, needs for facilitating production, and needs for enabling efficient use of materials.

It is desired to provide an open-type absorbent hygiene article which may fulfil one or more of the above-mentioned needs.

SUMMARY

Such an article is provided by an article as defined by the appended claim 1.

As such, there is provided a disposable open-type absorbent hygiene article having a longitudinal direction and a transverse direction, perpendicular to the longitudinal direction, and comprising an absorbent assembly. The absorbent assembly has a first portion and a second portion and opposing side edges extending in the longitudinal direction from the first portion to the second portion. The absorbent assembly further comprises two elastic side portions arranged at the second portion of the absorbent assembly, with an elastic side portion extending beyond each of the side edges of the absorbent assembly in the transverse direction of the article, so as to be configured to contact and be fastened to the first portion of the absorbent assembly when the absorbent article is worn.

Each one of the elastic side portions carries a fastener, the fastener at least partly overlapping the side portion, defining an overlapping region between the fastener and the elastic side portion. The article further comprises a reinforcement material patch for each elastic side portion the reinforcement material patch being permanently attached to the elastic side portion. The fastener is permanently attached to the reinforcement material patch in the overlapping region.

The reinforcement material patch hence reinforces the elastic side portion where the fastener is attached. This may facilitate reliable attachment of the fastener to the elastic side portion. Alternatively or additionally, the provision of a reinforcement material patch may enable selection between a wider range of materials for the elastic side portion. Alternatively or additionally, the provision of a reinforcement material patch may assist in distributing the pull force when pulling the fastener to extend the elastic side portion for fastening towards the front portion of the absorbent assembly.

The reinforcement material patch may be a piece of material which is free from connection to any other part of the absorbent article, but to the elastic side portion and the fastener.

The reinforcement material patch may extend at least partly over the overlapping region.

The reinforcement material patch may be arranged to remain in a substantially fixed position in relation to the elastic side portion, when the fastener is pulled. I.e. the reinforcement material patch is not intended to be folded out or away from the elastic side portion when the fastener is pulled.

The absorbent assembly may comprise a top sheet, a back sheet, and an absorbent core positioned between the top sheet and back sheet.

The fastener may be attached to the reinforcement material patch by a first joint, and the reinforcement material patch and/or the fastener may be attached to the elastic side portion by a second joint.

The first and/or second joints may at least partly extend in the overlapping region.

The first and second joints may be at least partly overlapping. For example, the first and second joints may be completely overlapping. As such, maintaining the reinforcement material patch in substantially fixed location in relation to the elastic side portion when the fastener is pulled may be facilitated.

In the overlapping region, the fastener may be located between the reinforcement material patch and the elastic side portion. This may provide for secure attachment of the fastener to the elastic side portion. Also, this may enable folding the fastener towards the reinforcement material patch, such that any fastening element (e.g. hooks/loops or adhesive) carried by the fastener is folded towards the reinforcement material patch rather than to the surface of the elastic side portion per se.

A first surface of the fastener may be attached to the reinforcement material patch by the first joint, and a second surface of the fastener may be attached to the elastic side portion by the second joint. The second surface may be a surface opposite to the first surface, i.e. the first and second surfaces are opposite outer surfaces of the fastener.

The first joint and/or the second joint may be the same type of joint.

The first joint and/or the second joint may comprise an adhesive.

When the first joint and/or the second joint comprises an adhesive, the adhesive may be applied in a layer over the first and/or second surface of the fastener.

The fastener and the reinforcement material patch may be arranged on a garment facing side of the elastic side portion.

The elastic side portion may be non-elastic in the overlapping region. This may facilitate secure arrangement of the reinforcement material patch and/or the fastener in the overlapping region.

The elasticity of the elastic side portion may be disabled in the overlapping region. For example, when the elastic side portion comprises elastic threads, the elastic threads may be cut or welded in the overlapping region.

The elastic side portion may be elastic in an edge region extending in the transverse direction between a free edge of the side portion and the overlapping region. This may facilitate forming of a soft edge of the elastic side portion, transversely outside of the overlapping region.

A width of the edge region from the free edge of the side portion to the overlapping region may be 10 mm or less. For example, the width may be within the range of from 2 to 8 mm. For example, the width may be within the range of from 3 to 7 mm.

The article may comprise an elastic belt panel, the elastic belt panel being permanently attached to the second portion of the absorbent assembly and extending beyond the side edges of the absorbent assembly in the transverse direction of the article, so as to form the elastic side portions. As such, an elastic belt panel extending over the back and sides of the wearer may provide for increased comfort and fit, as the elastic back panel adapts to the wearer's body and movements. The elastic back panel may be repeatedly stretched and retracted.

The elastic belt panel may be constituted by a continuous piece of elastic material. A continuous piece of elastic material may be advantageous in view of comfort and fit.

The side portions or the elastic belt panel forming the side portions may comprise an elastic material comprising elastic threads.

The reinforcement material patch may be constituted by a nonwoven material, for example it may be a single sheet of a nonwoven material. For example, the reinforcement material patch may have a basis weight within the range of from 30 to 100 gsm. For example, the reinforcement material patch may have a basis weight within the range of from 50 to 80 gsm.

In the overlapping region, the fastener may have a longitudinal extension being within the range of from 80 to 100% of the longitudinal extension of the elastic side portion at the overlapping region. This may facilitate pulling the elastic side portion along with pulling the fastener.

The fastener may have a longitudinal extension being within the range of from 90 to 100% of the longitudinal extension of the elastic side portion at the overlapping region.

The fastener may have a longitudinal extension being about 100% of the longitudinal extension of the elastic side portion at the overlapping region.

In the overlapping region, the fastener may have a longitudinal extension being within the range of from 80 to 100% of the longitudinal extension of the free edge of the elastic side portion. This may facilitate pulling the elastic side portion along with pulling the fastener.

The fastener may have a longitudinal extension being within the range of from 90 to 100% of the longitudinal extension of the free edge of the elastic side portion.

The fastener may have a longitudinal extension being about 100% of the longitudinal extension of the free edge of the elastic side portion.

The fastener may be a mechanical fastener. For example, the fastener may comprise hooks and/or loops. For example, the fastener may comprise a mechanical fastener material carrying hooks and/or loops. For example, the fastener may comprise a flap carrying hooks and/or loops.

When the article is in an initial state to be presented to a user, the fastener may be in a folded position wherein the fastener element contacts the reinforcement patch.

The transverse extension of the first portion of the absorbent assembly may be within the range of from 400 to 600 mm. The back panel may have a longitudinal length within the range of from 80 to 150 mm. The transverse extension of the back panel when in a stretched out condition may be within the range of from 150 to 250% of the transverse extension of the first portion of the absorbent assembly. For example, within the range of from 180 to 230%, or in another example within the range of from 190 to 215%.

The transverse extension of the first portion may be measured at the location where the elastic side portions are to be fastened to the first portion of the absorbent assembly. For example, this may be at the location of a landing zone for the fastening elements provided at the side portions.

In the context of the present disclosure, a longitudinal length is to be understood as the longest length of a specified part or sub part in the longitudinal direction. Analogously, a transverse width is to be understood as the widest width of specified part or sub part in the transverse direction.

For the purposes of the present disclosure, and unless otherwise explicitly mentioned, lengths, widths and other dimensions of a disposable absorbent hygiene product are measured with the disposable absorbent hygiene product in a relaxed flattened out state on a flat surface with any contracting elements being deactivated

BRIEF DESCRIPTION OF THE DRAWINGS

With reference to the appended drawings, below follows a more detailed description of variants of the open-type absorbent articles cited as examples.

DETAILED DESCRIPTION

Figure 1:
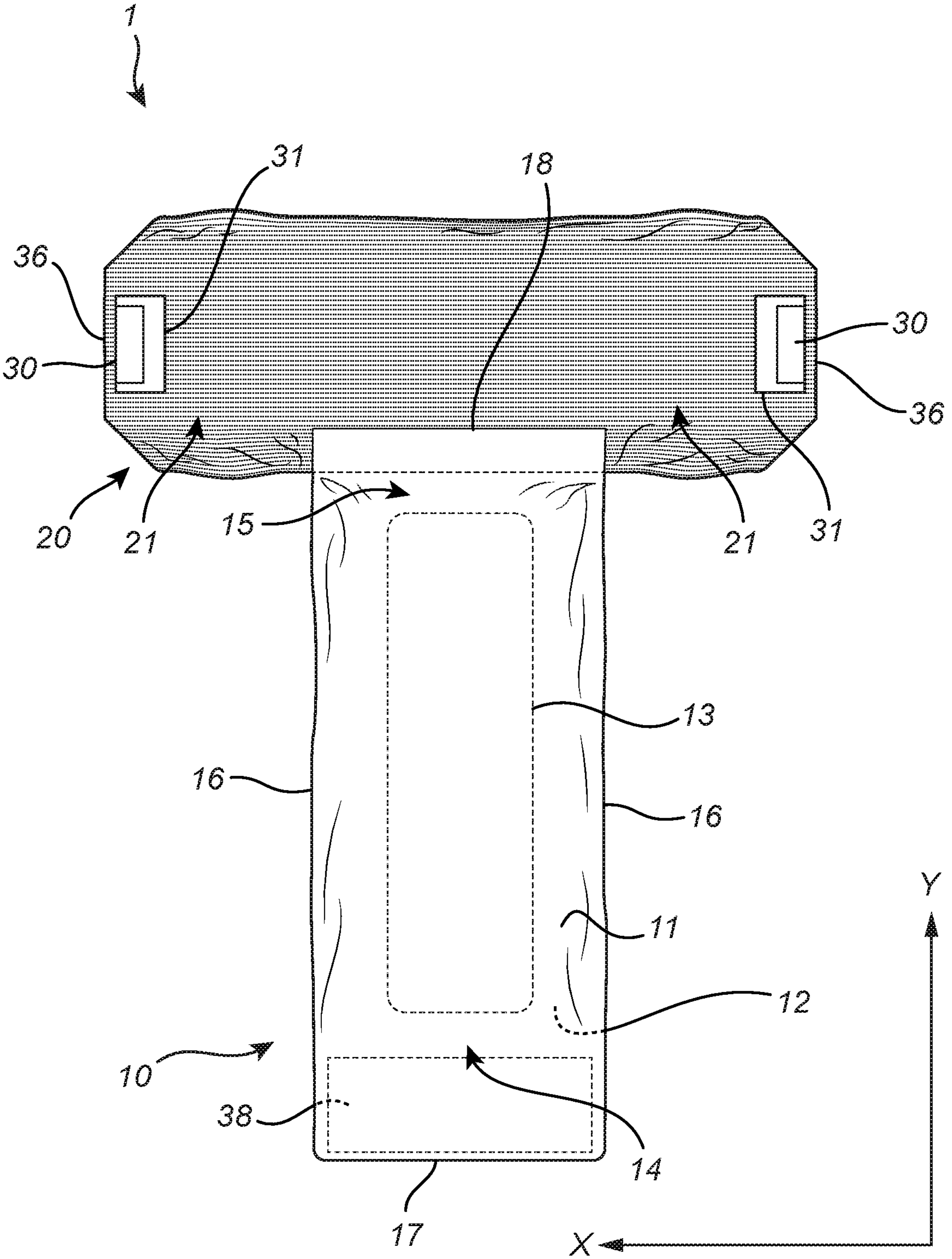
FIG. 1 is a schematic illustration of an open-type article having elastic side portions as seen from a garment-facing side.

The following description relates to an absorbent article 1 being a baby diaper. The diaper should be seen as an example of a disposable open-type absorbent article which may comprise an absorbent assembly 10 and elastic side portions 21 such as illustrated in FIG. 1. However, the present disclosure may be implemented in a plurality of different types of disposable open-type absorbent articles such as adult diapers, incontinence garments and the like.

FIG. 1 illustrates a disposable open-type absorbent article 1 having a longitudinal direction y and a transverse direction x, perpendicular to the longitudinal direction y. The article 1 also has a height direction perpendicular to the longitudinal direction y and transverse direction x.

In the context of the present disclosure "disposable" is used in its ordinary sense to mean an article that is disposed or discarded after a limited number of usage events over varying lengths of time, for example, less than 10 events, less than about 5 events, or after 1 event.

The article 1 is an open-type absorbent article meaning that it is provided in an open state (as illustrated in FIG. 1) to a user, and is closed to form a waist opening and two leg openings when applied to a wearer.

The article 1 comprises an absorbent assembly 10, and an elastic back panel 20.

The absorbent assembly 10 has a first portion 14 and a second portion 15 and opposing side edges 16 extending in the longitudinal direction Y from the first portion 14 to the second portion 15.

The first portion 14 is intended to be at the front (belly) waist region of the user, and the second portion 15 intended to be in the back region of the user when the article 1 is worn. The absorbent assembly 10 extends longitudinally between an assembly first edge 17 and an assembly second edge 18, wherein the assembly first edge 17 is intended to be directed towards the front of the user, and the assembly second edge 18 is intended to be directed towards the back of the user.

The absorbent assembly 10 may comprise a top sheet 11, a back sheet 12, and an absorbent core 13 positioned between the top sheet 11 and back sheet 12.

The back sheet 12 may typically be a liquid impermeable back sheet 12 at the garment facing side of the absorbent assembly 10. Materials suitable as back sheets are commonly known in the art of disposable absorbent hygiene products. The back sheet 12 may preferably be substantially impermeable to liquids such as urine. The back sheet may be breathable, i.e. gas permeable, implying that air and other gases may pass through the back sheet 12, while being substantially impermeable to liquids. For the purposes of the present disclosure, any material commonly known for use as back sheet materials may be included in the backsheet, including but not limited to polymeric films, hydrophobized nonwoven materials, fluid impermeable foams and fluid impermeable laminates. The back sheet may comprise one or more layers of material.

The top sheet 11 may typically be a liquid permeable top sheet 11 at the body facing side of the absorbent assembly 10. Materials suitable for top sheet 11 are commonly known in the art of disposable absorbent hygiene products, and for the purposes of the present disclosure any material commonly known for use as top sheet materials may be used, including, but not limited to woven materials, non-woven materials, perforated polymeric films, open cell foams, or combinations or laminates of these materials. The top sheet 11 may suitably be sufficiently fluid permeable to allow discharged body fluids such as urine to penetrate through the thickness of the top sheet 11. Also, the top sheet 11 is suitably manufactured from a material which is compliant and soft-feeling to the skin of the wearer.

The absorbent core 13 may comprise any suitable absorbent material, for example cellulosic fibers and/or superabsorbent polymers.

In the disposable absorbent article 1, the top sheet 11 and the back sheet 12 may extend outside the outer contour of the absorbent core 13 and be joined together outside the absorbent core 13 contour using methods commonly known in the art such as gluing or welding by means of heat or ultrasound.

Further, the absorbent assembly 10 may comprise one or more additional layers such as an acquisition layer or a distribution layer.

The absorbent assembly 10 may further display any additional features as used in the art, such as for example raised elastic members, commonly known as standing gathers. The absorbent assembly 10 may also be provided with a wetness indicator.

The article 1 of FIG. 1 comprises an elastic belt panel 20 being permanently attached to the second portion 15 of the absorbent assembly 10 and extending beyond the side edges 16 of the absorbent assembly 10 in the transverse direction X of the article 1, so as to form two elastic side portions 21 extending beyond each of the side edges 16 of the absorbent assembly 10 in the transverse direction X of the article 1.

In a non-illustrated alternative, two separate elastic side portions 21 may be arranged at the second portion 15 of the absorbent assembly, with each elastic side portion extending beyond the respective side edge 16 of the absorbent assembly.

In either case, the side portions 21 are configured to contact and be fastened to the first portion 14 of the absorbent assembly 10 when the absorbent article 1 is worn.

When worn, it is intended that the first portion 14 of the absorbent article 1 will be directed towards the front of the wearer, with the top sheet 11 facing the wearer.

Each of the elastic side portions 21 carries at a fastener 30 configured to perform the fastening of the side portions 21 to the first portion 14 of the absorbent assembly 10. The fastener 30 may be configured to be fastened to a corresponding landing zone 38 arranged at the back sheet side of the first portion 14 of the absorbent assembly 10.

The fastener 30 may, as in the variant illustrated in FIG. 1, be arranged on the body-facing side of the elastic side portion 21.

Figure 2A:
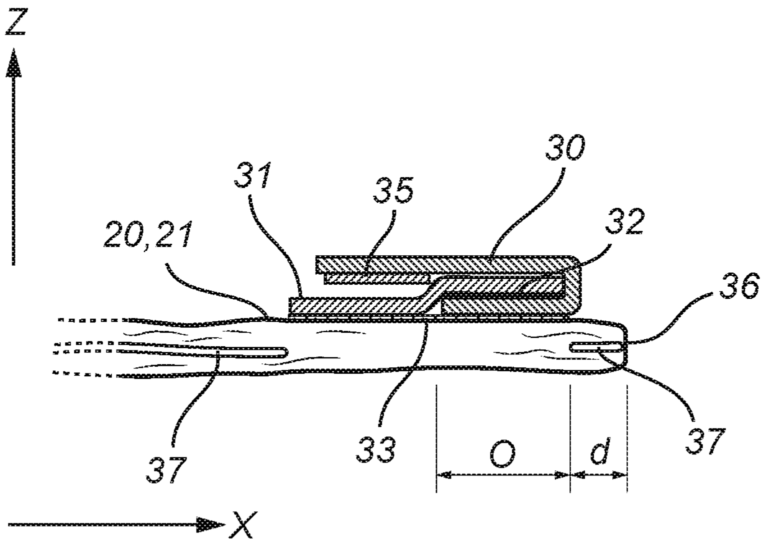
FIG. 2*a* is a schematic illustration as seen in a cross-section from the longitudinal direction Y of an elastic side portion carrying a reinforcement patch and a fastener in a folded state.

FIG. 2*a* illustrates a cross-section seen along the transverse direction X of an elastic side portion 21 in FIG. 1.

As shown in FIG. 2*a*, the fastener 30 at least partly overlaps the elastic side portion 21, defining an overlapping region O between the fastener 30 and the elastic side portion 21. A reinforcement material patch 31 is permanently attached to the elastic side portion 21, and a portion of the reinforcement material patch 31 is present in the overlapping region O. The fastener 30 is permanently attached to the reinforcement material patch 31 in the overlapping region O.

As illustrated in FIG. 2*a* the fastener 30 may be attached to the reinforcement material patch 31 by a first joint 32, and the reinforcement material patch 31 attached to the elastic side portion 21 by a second joint 33.

As such, the first and second joint may be applied in subsequent steps of a manufacturing procedure. For example, the fastener may be attached to the reinforcement material patch by the first joint in a first step, and the reinforcement material patch carrying the fastener may be attached to the elastic side portion by a second joint as a second step.

The first and/or second joint may be formed by any suitable attachment known in the art. For example, the first and/or second joint may be a welded joint. Alternatively or additionally, the first and/or second joint may be an adhesive joint.

As exemplified in FIG. 2*a*, the first and second joints 32, 33 may be least partly overlapping. Accordingly, it may be ensured that the reinforcement patch and the fastener 30 are maintained in a fixed position in relation to the elastic side portion 21.

As exemplified in FIG. 2*a*, in the overlapping region O, the fastener 30 may be located between the reinforcement material patch 31 and the elastic side portion 21. This may facilitate production as mentioned in the above, since the fastener 30 may be attached to the reinforcement material patch 31 in a first step, and the assembly of the fastener 30 and the patch 31 may then be attached to the elastic side portion 21 in a second step.

In another, non-illustrated variant, the reinforcement material patch 31 may be located between the elastic side portion 21 and the fastener 30.

The reinforcement material patch may be selected so as to provide the necessary reinforcement to the side portion 21 to secure the fastener 30. For example, the reinforcement material patch may be constituted by a nonwoven material. The reinforcement material patch may be a single sheet of material. This provides for a simple and easy construction. For example, the reinforcement material patch may have a basis weight of 30 to 100 gsm, such as 50 to 80 gsm.

It is to be understood that the purpose of the patch 31 is to strengthen the material of the side portion 21 at the attachment of the fastener 30. The patch 31 may also provide for convenient attachment solutions for the fastener 30. It is therefore intended that the patch 31 should be confined to an area of attachment of said fastener 30. The term reinforcement patch 31 is thus not to encompass any layers extending e.g. over the entire area of the side portion 21.

The fastener 30 may comprise a fastening element 35 configured to accomplish the fastening to the first portion 14 of the absorbent assembly 10, for example to a landing zone 38 thereof. The fastening element 35 may comprise e.g. an adhesive fastening element, for example an adhesive or a tape. The fastening element 35 may comprise e.g. a mechanical fastening element, for example the fastening element 35 may comprise hooks and/or loops.

As illustrated in FIG. 2*a*, the fastener 30 may assume a folded position in which the fastener is folded such that the fastening element 35 faces the reinforcement material patch 31. Accordingly, the elastic side portion 21 need not contact the fastening element. Instead, the material of the reinforcement material patch 31 may be configured to allow release of the fastener element 35 from the reinforcement material patch 31 when a user grasps the fastener 30 for applying the article 1 to a wearer.

For example, the fastener 30 may comprise a fastening element 35 in the form of a hook material.

The landing zone 38 on the first portion 14 of the absorbent assembly may for example have an extension along the transverse direction X allowing for adjusting the fastening of the fastening element 35 to the needs of the wearer.

As illustrated in FIG. 2*a*, a first surface of the fastener 30 may be attached to the reinforcement material patch 31 by the first joint 32, and a second surface of the fastener 30 may be attached to the elastic side portion 21 by the second joint 33.

As illustrated, the first joint 32 and/or the second joint 33 may comprise an adhesive. The adhesive may be applied in a layer over the first and/or second surface of the fastener 30.

As exemplified in the illustrated article, the elastic side portion 21 may be non-elastic in the overlapping region (O). This may facilitate the joining of the reinforcement material patch 31 and the fastener to the elastic side portion 21.

The elasticity of the elastic side portion 21 may be disabled in the overlapping region (O). For example, the elastic side portion 21 may be made from an elastic material, wherein the elasticity is removed or disabled in the overlapping region.

In an example, the elastic side portion 21 may be made by a material comprising elastic threads 37. The elastic threads may be removed or disabled in the overlapping region O. To disable the elastic threads 37, they may e.g. be cut. To ensure that the elasticity remains in the elastic side portion 21 outside of the overlapping region O, the ends of the elastic threads 37 may for example be welded at the borders of the overlapping region O.

As in the illustrated article 1, the elasticity of the side portion 21 may be disabled in substantially the entire area of the side portion 21 overlapping the reinforcement material patch 31, which may extend beyond the overlapping region O.

As in the illustrated article 1, the elastic side portion 21 may be elastic in an edge region extending in the transverse direction X between a free edge 36 of the side portion 21 and the overlapping region O. Accordingly, the edge region of the elastic side portion 21 between the free edge 36 and the overlapping region O may retract and form a contracted edge, which may provide for softness and increased comfort to the wearer.

Figure 2B:
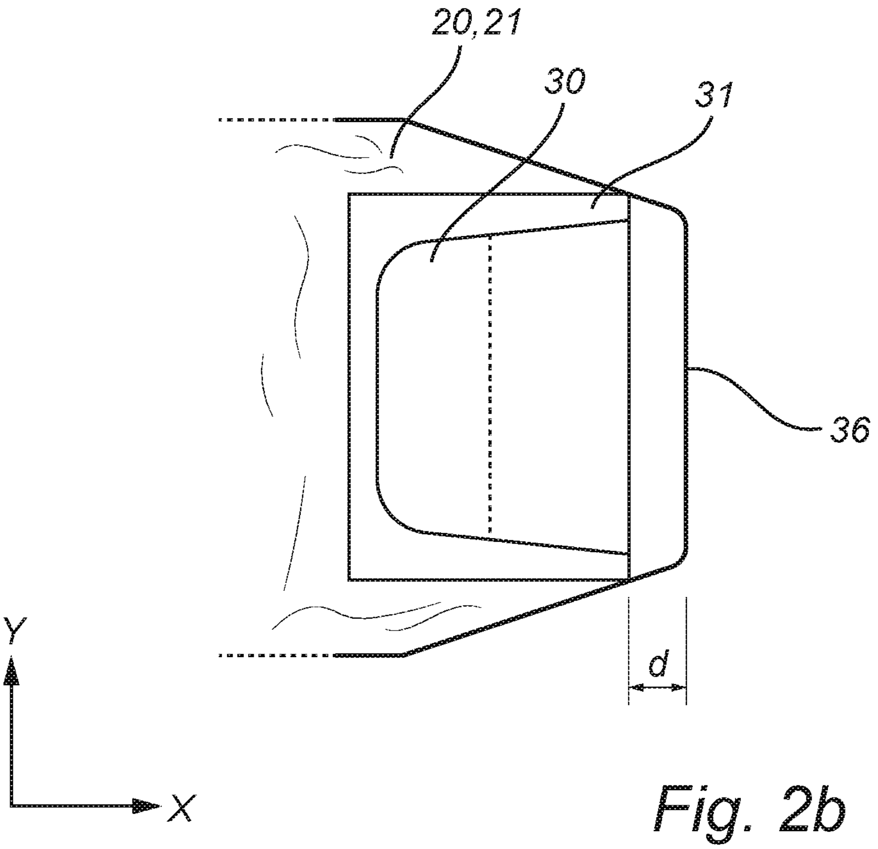
FIG. 2*b* is a schematic illustration of the elastic side portion of FIG. 2*a* as seen from the garment-facing side of the article.

FIG. 2*b* illustrates the elastic side portion 21 of FIG. 2*a* from the garment facing side of the article 1. The edge region between the free edge 36 and the overlapping region O is illustrated in an outstretched state. In a released state, the edge region would contract towards the fastener 30.

A width d of the edge region from the free edge 36 of the side portion 21 to the overlapping region O may be less than 10 mm. For example, the width d may be in the range 2 to 8 mm, or in the range 3 to 7 mm.

Figure 3A:
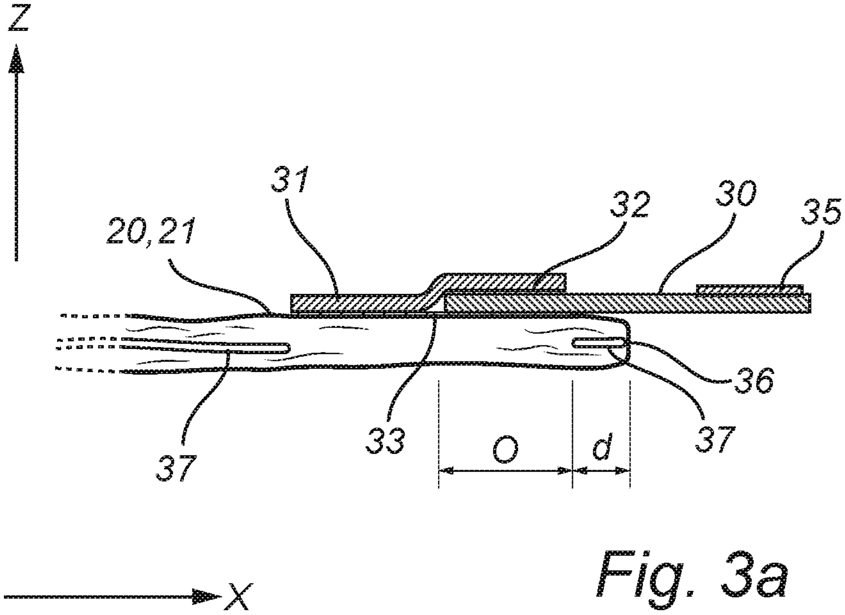
FIG. 3*a* is a schematic illustration of the elastic side portion of FIG. 2*a* in a folded-out state.
Figure 3B:
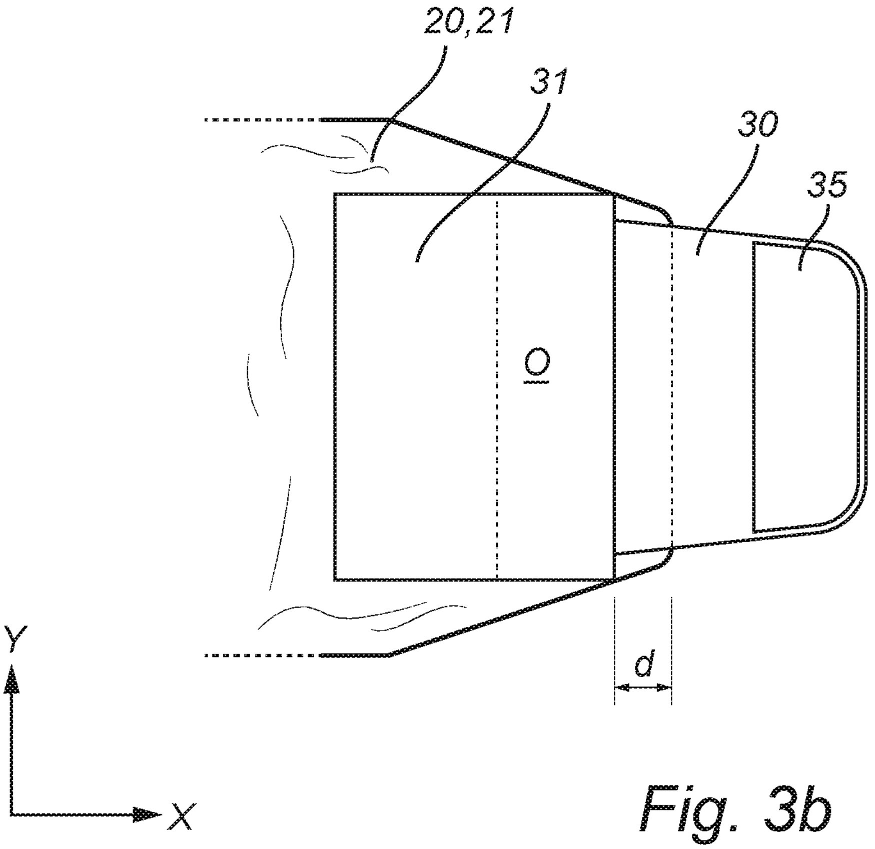
FIG. 3*b* is a schematic illustration of the elastic side portion of FIG. 2*b* in a folded-out state.

FIGS. 3*a* and 3*b* correspond to FIGS. 2*a* and 2*b*, respectively, but showing the elastic side portion 21 with the fastener 30 in a folded-out state, such as before fastening the article 1 around the waist of a wearer.

In some variants, such as in the illustrated example, the elastic side portions 21 may be formed by an elastic belt panel 20. The elastic belt panel 20 is constituted by a continuous piece of elastic material. This may facilitate distribution of forces around the waist of the wearer and provide for a snug and comfortable fit.

In some variants, such as in the illustrated article 1, in the overlapping region O, the fastener 30 may have a longitudinal extension being in the range 80 to 100% of the longitudinal extension of the free edge 36 of the elastic side portion 21. For example, the extension may be in the range 90 to 100% of the longitudinal extension of the free edge 36 of the elastic side portion 21. As in the illustrated article, the extension may be about 100% of the extension 36 of the free edge of the elastic side portion 21.

The fastener 30 may hence assist in holding out the longitudinal extension y of the elastic side portion 21 when the article 1 is worn, which provides for increased comfort and a satisfactory function of the side portions 21. When the article 1 comprises an elastic belt panel 20, the fasteners 30 applied on both side portions 21 formed by the elastic belt panel 20 may contribute to distributing the forces through the belt panel in an efficient manner.

As in the illustrated variant, the fastener 30 may be tapering inward towards the outer transverse end thereof, such that the fastener 30 is more narrow as seen along the longitudinal direction Y at the outermost end of the fastener 30 than at the attachment to the elastic side portion 21. The portion of the fastener 30 being attached to the elastic side portion 21 may still have the desired extension along the longitudinal direction Y as mentioned in the above.

In view of the above-mentioned description of an exemplary absorbent article, it will be understood that many variants and options are available within the scope of the present disclosure.

The invention claimed is:

1. A disposable open-type absorbent hygiene article defining a longitudinal direction and a transverse direction perpendicular to the longitudinal direction and comprising:

an absorbent assembly; and an elastic belt panel, wherein the absorbent assembly comprises a first portion, a second portion, and opposing side edges extending in the longitudinal direction from the first portion to the second portion, wherein the elastic belt panel is attached to the second portion of the absorbent assembly, wherein the elastic belt panel comprises an elastic side portion extending beyond one of the side edges of the absorbent assembly in the transverse direction, wherein the elastic side portion is configured to contact and be fastened to the first portion of the absorbent assembly when the absorbent article is worn, wherein the elastic side portion carries a fastener with an overlapping region between the fastener and the elastic side portion, wherein the overlapping region is defined as a region in which the fastener is attached to an upper surface of the elastic side portion, wherein a reinforcement material patch is permanently attached to the elastic side portion, wherein the fastener is permanently attached to the reinforcement material patch in the overlapping region, wherein the fastener is permanently attached to the upper surface of the elastic side portion at a first position, wherein the reinforcement material patch is permanently attached to the upper surface of the elastic side portion at a second position, and wherein the first position and the second position are adjacent to each other in the transverse direction.

2. The disposable open-type absorbent hygiene article according to claim 1, wherein the fastener is attached to the reinforcement material patch by a first joint, and the reinforcement material patch and the fastener is attached to the elastic side portion by a second joint.

3. The disposable open-type absorbent hygiene article according to claim 2, wherein the first and second joints are at least partly overlapping.

4. The disposable open-type absorbent hygiene article according to claim 3, wherein a first surface of the fastener is attached to the reinforcement material patch by the first joint, and a second surface of the fastener is attached to the elastic side portion by the second joint.

5. The disposable open-type absorbent hygiene article according to claim 4, wherein the first joint and/or the second joint comprises an adhesive, and wherein the adhesive is applied in a layer over the first and/or second surface of the fastener.

6. The disposable open-type absorbent hygiene article according to claim 2, wherein the elastic belt panel comprises elastic threads on both sides of the second joint along the transverse direction.

7. The disposable open-type absorbent hygiene article according to claim 1, wherein, in the overlapping region, the fastener is located between the reinforcement material patch and the elastic side portion.

8. The disposable open-type absorbent hygiene article according to claim 1, wherein the elastic side portion is non-elastic in the overlapping region.

9. The disposable open-type absorbent hygiene article according to claim 1, wherein the elastic side portion is elastic in an edge region extending in the transverse direction between a free edge of the elastic side portion and the overlapping region.

10. The disposable open-type absorbent hygiene article according to claim 9, wherein a width of the edge region from the free edge of the elastic side portion to the overlapping region is 10 mm or less.

11. The disposable open-type absorbent hygiene article according to claim 9, wherein the width is within a range of from 2 to 8 mm.

12. The disposable open-type absorbent hygiene article according to claim 9, wherein the width is within a range of from 3 to 7 mm.

13. The disposable open-type absorbent hygiene article according to claim 1, wherein the elastic belt panel is permanently attached to the second portion of the absorbent assembly.

14. The disposable open-type absorbent hygiene article according to claim 1, wherein the elastic belt panel is formed by a continuous piece of elastic material.

15. The disposable open-type absorbent hygiene article according to claim 1, wherein the elastic side portion comprises an elastic material comprising elastic threads.

16. The disposable open-type absorbent hygiene article according to claim 1, wherein the reinforcement material patch is formed by a nonwoven material.

17. The disposable open-type absorbent hygiene article according to claim 1, wherein, in the overlapping region, the fastener has a longitudinal extension within a range of from 80 to 100% of the longitudinal extension of a free edge of the elastic side portion.

18. The disposable open-type absorbent hygiene article according to claim 17, wherein the fastener has a longitudinal extension within a range of from 90 to 100% of the longitudinal extension of the free edge of the elastic side portion.

19. The disposable open-type absorbent hygiene article according to claim 1, wherein the fastener is a mechanical fastener.

20. The disposable open-type absorbent hygiene article according to claim 1, wherein the first position is spaced from the second position along the transverse direction.

21. The disposable open-type absorbent hygiene article according to claim 1, wherein an entirety of the fastener and an entirety of the reinforcement material patch are positioned above the upper surface of the elastic side portion.

22. A disposable open-type absorbent hygiene article defining a longitudinal direction and a transverse direction perpendicular to the longitudinal direction and comprising:

an absorbent assembly, wherein the absorbent assembly comprises a first portion, a second portion, and opposing side edges extending in the longitudinal direction from the first portion to the second portion, two elastic side portions arranged at said second portion of the absorbent assembly and extending beyond the side edges of the absorbent assembly in the transverse direction, wherein the two elastic side portions are configured to contact and be fastened to the first portion of the absorbent assembly when the absorbent article is worn, wherein each of the two elastic side portions carries a fastener with an overlapping region therebetween, wherein the overlapping region is defined as a region in which the fastener is attached to an upper surface of the elastic side portion, wherein a reinforcement material patch is permanently attached to each of the two elastic side portions, with the fastener positioned therebetween in the overlapping region, wherein, for each of the two elastic side portions, the fastener is permanently attached to the reinforcement material patch in the overlapping region, wherein the fastener is permanently attached to the upper surface of the elastic side portion at a first position, wherein the reinforcement material patch is permanently attached to the upper surface of the elastic side portion at a second position, and wherein the first position and the second position are adjacent to each other in the transverse direction.

23. The disposable open-type absorbent hygiene article according to claim 22, wherein an entirety of the fastener and an entirety of the reinforcement material patch are positioned above the upper surface of the elastic side portion.

* * * * *